United States Patent [19]

Reuschling et al.

[11] 4,079,145

[45] Mar. 14, 1978

[54] CERTAIN PYRROLIDONE DERIVATIVES AND PHARMACEUTICAL USE THEREOF

[75] Inventors: Dieter-Bernd Reuschling, Butzbach; Klaus Kühlein; Bernward Schölkens, both of Kelkheim, Taunus; Rudolf Kunstmann, Breckenheim, Taunus; Ulrich Lerch, Hofheim, Taunus; Wilhelm Bartmann, Neuenhain, Taunus; Hermann Teufel, Kelkheim, Taunus; Gerhard Beck, Frankfurt am Main, all of Germany

[73] Assignee: Hoechst Aktiengesellschaft, Frankfurt am Main, Germany

[21] Appl. No.: 698,491

[22] Filed: Jun. 22, 1976

[30] Foreign Application Priority Data

Jun. 24, 1975 Germany .................. 2527989
Jun. 24, 1975 Germany .................. 2527990
Jun. 24, 1975 Germany .................. 2528037

[51] Int. Cl.$^2$ .................................. C07D 207/26
[52] U.S. Cl. ..................... 424/274; 260/326.5 FL; 260/326.45; 542/426; 542/427; 542/429; 542/430; 542/438

[58] Field of Search ............ 260/326.45, 326.2, 240 L, 260/240 E; 424/274

[56] References Cited

U.S. PATENT DOCUMENTS

| 3,192,206 | 6/1965 | Lunsford et al. | 260/326.45 |
| 3,192,207 | 6/1965 | Lunsford et al. | 260/326.45 |
| 3,192,221 | 6/1965 | Lunsford et al. | 260/326.45 |

OTHER PUBLICATIONS

Hoechst AG: Pyrrolidone Prostaglandin Analogues (6-11-74).
Ambrus et al.; Chem. Abs. vol. 84: 59286k (1975).

*Primary Examiner*—R. Gallagher
*Assistant Examiner*—Mary Vaughn
*Attorney, Agent, or Firm*—Curtis, Morris & Safford

[57] ABSTRACT

The present invention relates to pyrrolidones which are analogues of prostaglandins and to a process for their manufacture. The compounds of the invention have prostaglandin-like pharmacological properties and can therefore be used as pharmaceutical compositions.

3 Claims, No Drawings

CERTAIN PYRROLIDONE DERIVATIVES AND PHARMACEUTICAL USE THEREOF

The present invention relates to pyrrolidones and to a process for their manufacture.

The natural prostaglandins have a hydrocarbon skeleton of generally 20 carbon atoms. They are distinguished from one another by the number of hydroxyl groups and double bonds. Since they show a great variety of physiological effects at the same time and have only a short half-life value in the organism, their use as therapeutical agents is limited.

This is why it becomes more and more important to find prostaglandins having a longer half-life and showing a specific effect.

The present invention provides novel pyrrolidones which are analogues of prostaglandins and correspond to the formula

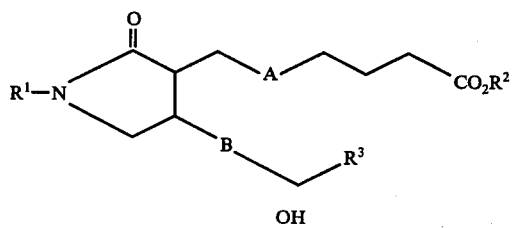

in which

A is a —CH$_2$—CH$_2$— group or a —C≡C— group;
B is a —CH$_2$—CH$_2$— group or a —CH=CH— group on the understanding that A represents only the —CH$_2$—CH$_2$— group, if B is the —CH$_2$—CH$_2$— group;
R$^1$ is a straight-chain or branched alkyl radical having from 1 to 6 carbon atoms or a cycloalkyl radical having from 3 to 7 ring members, the cycloalkyl radical optionally being substituted by straight-chain or branched (C$_1$-C$_4$)-alkyl or -alkoxy groups;
R$^2$ stands for hydrogen, a (C$_1$-C$_5$)-aliphatic hydrocarbon radical or a cycloaliphatic or araliphatic hydrocarbon radical having both from 3 to 8 carbon atoms;
R$^3$ represents a straight-chain or branched alkyl radical having from 1 to 10 carbon atoms which may be substituted by an O- or S-alkyl radical having from 1 to 5 carbon atoms, by a phenoxy radical optionally substituted by one or several optionally halogenated alkyl groups having from 1 to 3 carbon atoms, by halogen atoms or optionally halogenated phenoxy radicals, or by an O-furyl radical or an O-benzyl radical which may carry alkyl groups having from 1 to 3 carbon atoms as substituents, or by a trifluoromethyl radical, by a cycloalkyl radical having from 3 to 7 ring members, or by a phenyl or furyl radical which may be substituted by one or several alkyl groups having from 1 to 3 carbon atoms and in which the side chains, in the 3- and 4-position of the pyrrolidone ring, stand in the trans-position to each other, as well as the physiologically acceptable metal and amine salts of the free acids.

The invention also provides a process for the preparation of pyrrolidones of the formula I, which comprises
$a_1$. reacting a pyrrolidone of the formula

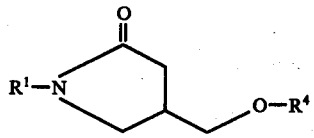

in which R$^1$ is defined as in formula I and R$^4$ represents a group which can easily be split off in an acid medium, in the presence of a base of the formula MeB    III, in which Me represents an alkali metal atom and B stands for hydrogen, a straight-chain or branched (C$_1$-C$_4$) alkoxy radical or the group

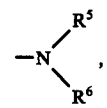

in which R$^5$ and R$^6$, which may be the same or different, stand for a (C$_1$-C$_6$) alkyl or a (C$_3$-C$_6$) cycloalkyl group, with an alkinyl halide of the formula

in which either Hal$^1$ represents bromine and Hal$^2$ is chlorine or Hal$^1$ stands for iodine and Hal$^2$ is bromine, or Hal$^1$ represents iodine and Hal$^2$ is chlorine, to yield a compound of the formula

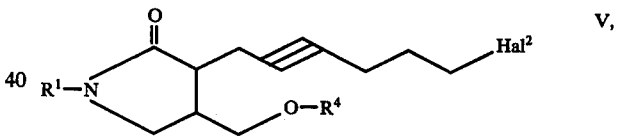

$a_2$. reacting the compound of the formula V obtained with an alkali metal cyanide, in which process the cyanoalkine of the formula

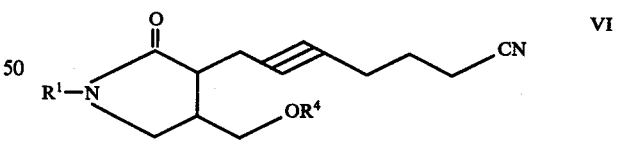

is obtained, in which R$^1$ and R$^4$ are defined as in the formula II above,
$a_3$. hydrolyzing the nitrile of the formula VI obtained in a basic medium to give an alkinic acid of the formula

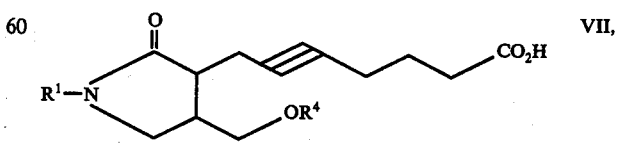

in which R$^1$ and R$^4$ are defined as in formula II above,
$a_4$. converting the compound of the formula VII obtained into the ester of the formula

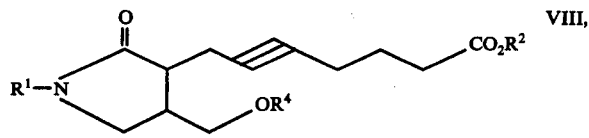

in which $R^1$ and $R^2$ are defined as in formula I, and $R^4$ is defined as in formula II, $a_5$. splitting off the protective group $R^4$ in a compound of the formula VIII under acid conditions, to yield an alcohol of the formula

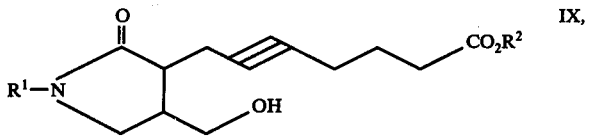

in which $R^1$ and $R^2$ are defined as in formula I, or $a_5'$. effecting the esterification of the compound of the formula VII as well as the splitting-off of the protective group $R^4$ in a single step, or $a_5''$. converting the nitrile group in the compound of the formula VI in an acid medium directly into an ester group, while the protective group $R^4$ is being split off at the same time, $a_6$. oxidizing the alcohol of the formula IX obtained, while obtaining an aldehyde of the formula

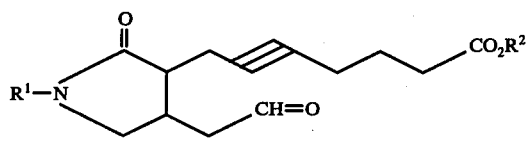

in which $R^1$ and $R^2$ are defined as in formula I, $a_7$. reacting the aldehyde of the formula X obtained with a phosphonate of the formula

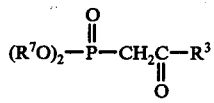

in which $R^3$ is defined as in formula I and $R^7$ represents an unbranched ($C_1$-$C_4$)alkyl radical, to yield a compound of the formula

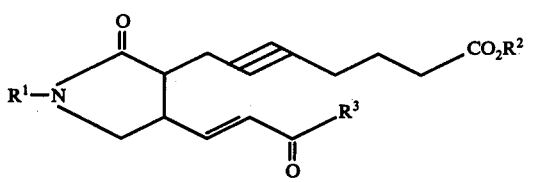

in which $R^1$, $R^2$ and $R^3$ are defined as in formula I, $a_8$. reducing the ketocarbonyl group in the compound of the formula XII obtained, in which process a compound of the formula I is obtained, wherein A represents the —C≡C— group and B stands for the —CH=CH— group, or $b_1$. reducing a pyrrolidone of the formula IX

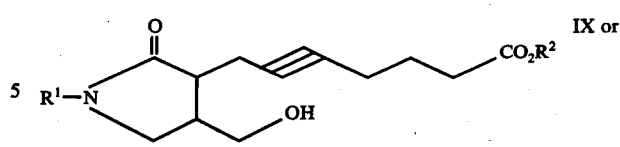

a pyrrolidone of the formula XIII

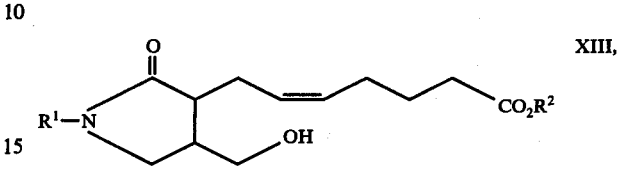

$R^1$ and $R^2$ being in each case defined as in formula I, to yield a compound of the formula XIV

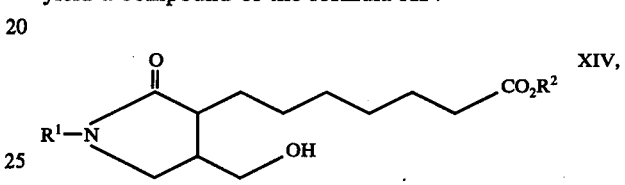

$b_2$. oxidizing the alcohol of the formula XIV obtained, in which process an aldehyde of the formula XV

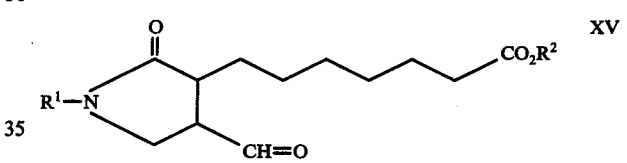

is obtained, in which $R^1$ and $R^2$ are defined as in formula I, $b_3$. reacting the aldehyde of the formula XV obtained with a phosphonate of the formula XI, wherein $R^3$ and $R^7$ are defined as in this formula, to give a compound of the formula XVI

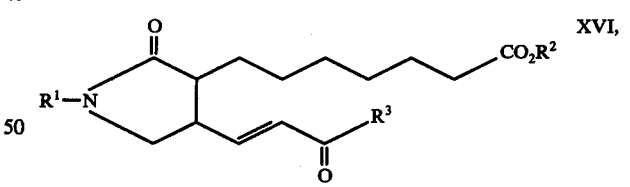

in which $R^1$, $R^2$ and $R^3$ are defined as in formula I, $b_4$. reducing the ketocarbonyl group in the compound of the formula XVI obtained, in which process a compound of the formula I is formed, wherein A represents the —$CH_2$—$CH_2$— group and B represents the —CH=CH— group, and optionally $c_1$. hydrogenating a compound of the formula I, in which A and/or B represent a —CH=CH— or —C≡C— group, to yield a compound of the formula I, in which A and B each represent a —$CH_2$—$CH_2$— group, or $c_2$. hydrogenating selectively a compound of the formula XII or XVI to give a compound of the formula XVII

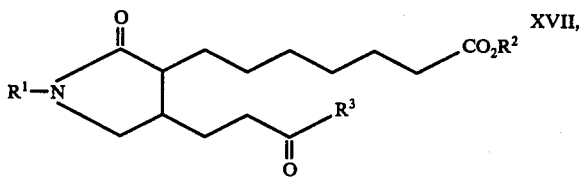

and reducing subsequently the ketocarbonyl group to give the hydroxyl group, in which process a compound of the formula I is obtained, wherein A and B each represent a —CH$_2$—CH$_2$— group, or optionally c$_3$. hydrogenating a compound of the formula XVIII

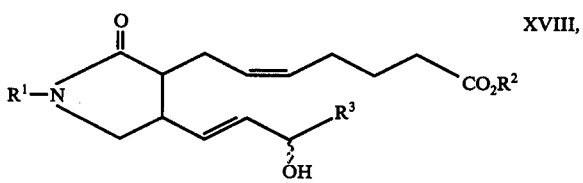

in which R$^1$, R$^2$ and R$^3$ are defined as in formula I, to yield a compound of the formula I, in which A and B each represent a —CH$_2$—CH$_2$— group, or c$_4$. hydrogenating a compound of the formula XIX

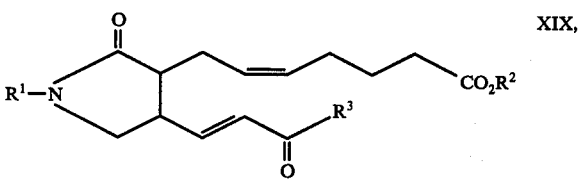

in which R$^1$, R$^2$ and R$^3$ are defined as in formula I, selectively to yield a compound of the formula XVII, and reducing subsequently the ketocarbonyl group to give the hydroxyl group, in which process a compound of the formula I is obtained, wherein A and B each represent a —CH$_2$—CH$_2$— group, and optionally converting the compound of the formula I obtained in a common manner into the free acid or the physiologically acceptable metal or amine salt thereof.

Preference is given to the following substituents:

Of the meanings given for R$^1$, straight-chain alkyl radicals having from 1 to 4 carbon atoms, the isopropyl and the tertiary butyl radical, cycloalkyl radicals having from 5 to 6 ring members optionally substituted by straight-chain (C$_1$-C$_3$)-alkyl or -alkoxy groups in particular the cyclohexyl and the cyclohexylmethyl radical; of the meanings given for R$^2$, preference is given to (C$_1$-C$_4$) alkyl radicals, preferably the methyl radical, furthermore, cycloalkyl radicals having from 5 to 7 carbon atoms and aralkyl radicals having from 7 to 8 carbon atoms, in particular the benzyl radical; of the meanings given for R$^3$, alkyl radicals having from 3 to 8 carbon atoms, cycloalkyl radicals having from 5 to 7 carbon atoms, as well as the phenyl radical or a phenyl radical substituted by one to three methyl groups. There are also preferred for R$^3$ those radicals of the formula —C(R')$_2$—CH$_2$—O—R", in which R' represents a (C$_1$-C$_3$) alkyl radical on the understanding that the two R' may be different, and in which R" represents a (C$_1$-C$_5$) alkyl radical, a phenyl radical which may be substituted by 1 or 2 fluorine, chlorine and/or bromine atoms, by the trifluoromethyl radical, by a phenoxy radical substituted in the p-position by F, Cl, Br or CF$_3$, or by one to three (C$_1$-C$_3$) alkyl radicals, or R" represents a benzyl radical which may be substituted by one to three (C$_1$-C$_3$) alkyl radicals.

The pyrrolidones of the formula II which have a hydroxymethyl function in the 4-position, as well as the pyrrolidones of the formula XIII, which have been used as starting compounds in the process of the invention, can be prepared according to German Offenlegungsschrift No. 2,452,536.

As protective groups for the hydroxymethylpyrrolidones, there are mentioned above all those groups which can be split off again under mild reaction conditions, for example, by acid hydrolysis or by hydrogenation.

These requirements are met in particular by the allyl, benzyl, tert.butyl and chloromethyl radicals, as well as by enol ether groups [E. J. Corey, J. W. Suggs, J. Org. Chem. 38, 3224 (1973); E. J. Corey, P. A. Grieco, Tetrah. Letters 107 (1972)]. Preference is given to acetals.

The process of the invention starts by deprotonizing the protected 4-hydroxymethylpyrrolidones of the formula II with an appropriate base MeB in the α-position to the carbonyl group and subsequently reacting them with an alkinyldihalide (IV), such as 1-iodo-6-bromo-hexine-(2), 1-iodo-6-chloro-hexine-(2) or, preferably, 1-bromo-6-chloro-hexine-(2).

The bases of the formula III are known in the literature. In this formula, Me represents an alkali metal, preferably lithium, sodium or potassium.

If B stands for the radical

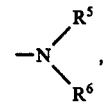

R$^5$ and R$^6$ are preferably straight-chain or branched (C$_1$-C$_6$) alkyl radicals, such as, for example, methyl, ethyl, propyl, pentyl, hexyl, preferably isopropyl, or in the case of a (C$_3$-C$_6$) cycloalkyl group, they may be, for example, cyclopropyl, cyclobutyl, cyclopentyl, in particular cyclohexyl.

Particularly preferred compounds of the formula III are sodium hydride, potassium-tert.-butylate, lithium-diisopropylamide and lithium-cyclohexylisopropylamide.

The reaction of the base (III) with the compounds of the formula II is carried out with the exclusion of air and moisture, since the bases and the resulting carbanions are sensitive to air and moisture. As solvents, especially aprotic polar liquids are mentioned which have a sufficient dissolving power also at low temperatures and which are inert under the reaction conditions. Where required, mixtures of two or more solvents are used to reduce the solidification point. Preference is given, for example, to ethers, such as dimethylether, diethylether, diisopropylether, tetrahydrofuran, glycol-dimethylether, furthermore, dimethylformamide, dimethylsulfoxide or toluene. The amounts of the solvents are to be calculated in such a way that there are homogeneous solutions present in each case.

The reaction temperatures are in a range of from −100° to +10° C, preferably from −80° to −20° C, in particular between −70° and −40° C. The reaction is generally carried out by adding a solution of the pyrrolidone of the formula II, while stirring, to a deep-frozen solution of the base (III) in one of the said solvents, so as to maintain the temperature range desired for the reaction. The components may also be added to one another vice versa. The deprotonization of the pyrrolidone is generally completed after about 30 minutes.

Subsequently the deep-frozen solution thus obtained is introduced into a deep-frozen solution of the alkinyl halide of the formula IV [lit.: A. J. Rachlin, N. Wasyliw and M. W. Goldberg, J. Org. Chem. 26, 2688, (1961)] again in a way that the abovementioned temperature range of the reaction mixture is not substantially exceeded as a result of the exothermic reaction. As solvent there may be used in each case one of the above-specified solvents.

After the addition, the mixture is continued to be stirred for half an hour to 12 hours at a low temperature, then it is slowly heated to room temperature and is then worked up.

The mixture may be worked up, for example, by adding a determined amount of water to the reaction mixture, separating the organic phase, and by drying and concentrating it. The residue can be purified by column chromatography. Often, however, the products are obtained already in such a pure state that a purification is not necessary.

In order to prepare the nitriles of the formula VI, an alkali metal cyanide is dissolved in a solvent mixture, such as ethanol/water, dimethylformamide/water, or preferably in pure dimethylsulfoxide, and the halogen compound of the formula V which is dissolved in the same solvent is added dropwise to the alkali metal cyanide solution at a temperature of from 60° to 120° C, in particular from 80° to 90° C. After the addition, the mixture is continued to be stirred for 2 to 8 hours at a temperature in the range of from 80° to 90° C. The nitriles of the formula VI are isolated, for example, by adding a determined amount of water to the reaction mixture and by extracting the aqueous phase with an organic solvent which is not miscible with water. In this process the products are obtained in such a pure state that they can be used in the following reaction steps without further purification.

The alkaline hydrolysis of the nitriles of the formula VI to give the carboxylic acids of the formula VII is carried out in accordance with the methods described in the art (cf. for example, "Organikum" by a group of authors, VEB Deutscher Verlag der Wissenschafter, Berlin 1967, p. 411). A solution of the nitrile is heated, for example, with twice the molar amount of an aqueous 25% sodium hydroxide solution, in an amount of ethanol sufficient for a homogeneous solution, for 10 to 20 hours at 80° C. Subsequently the mixture is acidified with a mineral acid, and the free carboxylic acid is extracted with an organic solvent which is not miscible with water.

The esters of the formula VIII and/or IX may be prepared according to analogous processes which have been described in literature. Thus, for example, the acids can be esterified with the corresponding alcohol in the presence of a strong acid, such as sulfuric acid, hydrochloric, acid, p-toluene-sulfonic acid, trifluoroacetic acid, and others, optionally in the presence of an entrainer for the resulting water. The alcohol is used in an excess amount in this case.

Under these conditions, the protective group $R^4$ is simultaneously split off, and the compounds of the formula IX are directly obtained.

In contradistinction thereto, esterification with alcohols in the presence of carbodiimides does not attack the protective group $R^4$. Also the reaction with diazo alkanes, preferably diazo methane, in an inert solvent, leads to the same result.

Inasfar as the carboxylic acids used for the esterification have not been purified, a chromatographic purification in the ester phase (IX) is recommended.

As it has been indicated above, the splitting-off reaction of the protective group $R^4$ and the esterification can be carried out in a single step. Alternatively, the esters of the formula VIII are heated to 50° – 80° C for about 30 minutes in an alcohol, such as methanol, ethanol or isopropanol, preferably $R^2OH$, in the presence of acid catalysts, to split off the protective group. Subsequently the product is neutralized, and the compound of the formula IX is isolated by extraction with an appropriate solvent, for example, methylene chloride, chloroform or diethylether.

The esters of the formula IX are obtained directly from the nitrile of the formula VI, if the latter is dissolved in an excess of an alcohol, the solution is saturated with dry hydrochloric acid gas at a temperature of from 5° to −20° C, preferably from 0° to −5° C, and the solvent and the excess hydrochloric acid are eliminated carefully in vacuo after about 2 to 4 hours, the product is again dissolved in alcohol, is adjusted with an aqueous alkali metal hydroxide solution of 33% strength to a pH value of from 1 to 4, preferably from 1 to 2, and is subsequently heated for 0.5 to 3 hours to a temperature of from 60° to 80° C. The isolation of the esters of the formula IX is carried out, for example, by eliminating the solvent and extracting the residue subsequently with an organic solvent. Subsequently, a chromatographic purification of the ester (IX) is recommended.

The oxidation of the compounds of the formula IX to yield the compounds of the formula X is effected by means of oxidizing agents which are common for the oxidation of aliphatic alcohols to give aldehydes. Some of these common methods have been described in Houben-Weyl, vol. 7/1, p. 159. Further appropriate oxidizing agents are the complex compounds formed from thioethers, such as dimethylsulfide or thioanisol, with chlorine or N-chlorosuccinimide [E. J. Corey, C. U. Kim, J. Amer. Chem. Soc. 94, 7586 (1972); E. J. Corey, C. U. Kim, J. Org. Chem. 38, 1233, (1973)]. The oxidation may also be carried out by means of dimethylsulfoxide under various conditions [W. W. Epstein, F. W. Sweat, Chem. Rev. 67, 247 (1967)].

A particularly preferred variant is the oxidation by means of the chromium trioxide-pyridine complex compound (J. C. Collins, Tetrah. Letters 1968, 3363). At first, the complex compound is prepared in an inert solvent, preferably methylene chloride, and at a temperature of from −10° to +10° C, a solution of the alcohol (IX) is added. The oxidation is effected rapidly and is usually completed after 5 to 30 minutes.

The aldehyde of the formula X may be used in the following process step without further purification. If necessary, the aldehyde is purified by column chromatography.

The reaction of the phosphonates of the formula XI with compounds of the formula X may be carried out under the conditions which are common for the Horner reaction, for example in ethers at room temperature. As ethers there may be mentioned preferably, diethylether, tetrahydrofuran, and dimethoxyethane. In order to ensure the completion of the reaction, the phosphonate is used in an excess amount. Usually, the reaction is completed after 1 to 5 hours at room temperature. The reaction product of the formula XII is then isolated from the reaction mixture according to common methods and is purified by column chromatography.

The phosphonates of the formula XI are either known [D. H. Wadsworth et al., J. Org. Chem. 30, 680 (1965)], or they may be prepared in a manner analogous to known methods.

The compounds of the formula I are obtained by treating the compounds of the formula XII with a reducing agent. The reduction can be effected with all reducing agents which permit a selective reduction of a keto group to give a hydroxyl group. Preferred reducing agents are complex metal hydrides, in particular boron hydrides, such as sodium-boron hydride, zinc-boron hydride or lithium-perhydro-9b-boron-phenalkylhydride [H. C. Brown, W. C. Dickason, J. Am. Chem. Soc. 92, 709 (1970)]. The reaction is usually carried out at a temperature in the range of from 0° to 50° C in a solvent which is inert towards the hydrides, such as diethylether, dimethoxy-ethane, dioxan, tetrahydrofuran, or diethylene-glycol-dimethylether. The diastereomers obtained in this reduction may be separated by means of the common methods, such as thick layer or column chromatography.

The hydrogenation of the compounds of the formulae II, IX and/or XII according to process step $b_1$) to yield the compounds of the formula XIV may be carried out with catalytic as well as by way of non-catalytic processes, as has been described in the art (Houben-Weyl: Methoden der Organischen Chemie, Georg Thieme Verlag, Stuttgart 1970, vol. 5/1a); preference is given to catalytic processes.

The process steps $b_2$) to $b_4$) are carried out in a manner analogous to that described for the process steps $a_6$) to $a_8$).

The hydrogenation of the compounds of the formula I, in which A and B each represent insaturated groups, as well as of the compounds of the formulae XII and/or XIX in accordance with the process steps $c_1$) to $c_4$) may be effected according to common methods which permit a selective hydrogenation of isolated C-C double bonds and C-C triple bonds. Preference is given to catalytic hydrogenation processes, in particular to those operating with precious metal catalysts, such as palladium or platinum. The hydrogenation is usually carried out at a temperature in the range of from 20° to 30° C.

The reduction of the keto carbonyl group in the compounds of the formulae XVII and/or XIX is carried out, as has been described in the process step $c_2$) and/or $c_4$).

The conversion of compounds of the formula I into the free acids is effected according to one of the common saponification methods.

The preparation of pharmacologically acceptable salts from the acids is carried out according to known methods. The acid is dissolved in a solvent, such as water, methanol, tetrahydrofuran, and is then neutralized with the corresponding inorganic or organic base; subsequently — if the salt does not precipitate — a solvent of an appropriate polarity is added, such as methanol, ethanol, dioxan, or the product is evaporated to dryness.

Of the inorganic bases, preference is given to the alkali metal and the alkaline earth metal hydroxides. Of the organic bases, there are to be mentioned primary, secondary and tertiary amines, such as methyl-, dimethyl-, trimethyl-, and phenylethylamine, ethylene diamine, allylamine, piperidine, morpholine and pyrrolidone. There may also be mentioned amines which still contain hydrophilic groups, for example, ethanolamine and ephedrine. As quaternary bases, preference is given, for example, to tetramethyl- and benzyltrimethylammonium hydroxide.

The esters of the formula I, the acids which are at their basis as well as the salts thereof show prostaglandin—like effects. The novel compounds show luteolytic properties, they are able to inhibit the secretion of gastric juice, and also have bronchospasmolytic and/or antihypertensive effects.

The compounds of the invention may also be used as intermediate products for the preparation of other substances having a prostaglandin effect.

The acids and salts and/or esters may be used in the form of their aqueous solutions or suspensions or as solutions in pharmacologically acceptable organic solvents, such as mono- or polyvalent alcohols, dimethylsulfoxide or dimethylformamide, also in the presence of pharmacologically acceptable polymer carriers, for example, polyvinyl pyrrolidone.

Pharmaceutical compositions are the usual galenic infusion or injection solutions as well as tablets, however, preferably locally administerable compositions, such as creams, emulsions, suppositories, or sprays.

The compounds may be used by themselves or in conjunction with other pharmacologically active substances, such as diuretics or antihyperglycemics.

The following dosage units and/or daily dosage units may be mentioned for the above indications:

| Bronchodilatatory effect (spray) | |
|---|---|
| Dosage unit: | 0.1 – 1000 μg |
| preferred: | 1 – 200 μg |
| daily dosage unit: | 0.1 – 10 mg |

| Antihypertensive effect | |
|---|---|
| Dosage unit: | 1 – 1000 μg |
| preferred: | 1 – 100 μg (parenterally - i.v.) |
| daily dosage unit: | 1 – 10 mg |
| Dosage unit: | 0.5 – 10 000 μg |
| preferred: | 1 – 5 000 μg (orally) |
| daily dosage unit: | 1 – 10 mg |

The above-mentioned doses for the antihypertensive effect correspond to the doses for the treatment of gastro-intestinal diseases.

The values indicated above were obtained by testing the compounds of the invention on guinea pigs (bronchodilatatory effect) and/or on dogs (antihypertensive effect).

The compounds of the formulae V, VI, VII, VIII, IX, X, XII, XIV, XV, XVI and XVII are novel valuable intermediate products for the preparation of compounds of the formula I.

Besides the compounds specified in the Examples, particularly the following compounds may be prepared in accordance with the invention:

1-Methyl-3-[6-carbomethoxy-2-hexinyl-(1)]-4-[3-(RS)-hydroxy-(E)-1-hexenyl-(1)]-pyrrolidone, 1-methyl-3-[6-carbomethoxy-2-hexinyl-(1)]-4-[3-(RS)-hydroxy-4,4-dimethyl-(E)-1-octenyl-(1)]-pyrrolidone, 1-methyl-3-[6-carbomethoxy-2-hexinyl-(1)]-4-[3-(RS)-hydroxy-3-cyclohexyl-(E)-1-propenyl-(1)]-pyrrolidone, 1-methyl-3-[6-carbomethoxy-2-hexinyl-(1)]-4-[3-(RS)-hydroxy-3-cycloheptyl-(E)-1-propenyl-(1)]-pyrrolidone, 1-methyl-3-[6-carbomethoxy-2-hexinyl-(1)]-4-[[3-(RS)-hydroxy-4-methyl-4-[4-(4-chlorophenoxy)-phenoxy]-(E)-1-butenyl-(1)]]-pyrrolidone, 1-methyl-3-[6-carbomethoxy-2-hexinyl-(1)]-4-[[3-(RS)-hydroxy-4,4-dimethyl-4-[4-(4-chlorophenoxy)-phenoxy]-(E)-1-butenyl-(1)]]-pyrrolidone, 1-methyl-3-[6-carbomethoxy-2-hexinyl-(1)]-4-[3-(RS)-hydroxy-5-ethylthio-(E)-1-pentenyl-(1)]-pyrrolidone, 1-methyl-3-[6-carbomethoxy-2-hexinyl-(1)]-4-[3-(RS)-hydroxy-4-(4-fluorophenoxy)-(E)-1-butenyl-(1)]-pyrrolidone, 1-methyl-3-[6-carbomethoxy-2-hexinyl-(1)]-4-[3-(RS)-hydroxy-4-(4-chlorophenoxy)-(E)-1-butenyl-(1)]-pyrrolidone, 1-methyl-3-[6-carbomethoxy-2-hexinyl-(1)]-4-[3-(RS)-hydroxy-4-(3-trifluoromethylphenoxy)-(E)-1-butenyl-(1)]-pyrrolidone, 1-methyl-3-[6-carbomethoxy-2-hexinyl-(1)]-4-[3-(RS)-hydroxy-4-(methyl-propionyl-amino)-(E)-1-butenyl-(1)]-pyrrolidone, 1-methyl-3-[6-carbomethoxy-2-hexinyl-(1)]-4-[3-(RS)-hydroxy-4,4-dimethyl-5-ethoxy-(E)-1-pentenyl-(1)]-pyrrolidone, 1-methyl-3-[6-carbomethoxy-2-hexinyl-(1)]-4-[3-(RS)-hydroxy-4,4-dimethyl-5-methoxy-(E)-1-pentenyl-(1)]-pyrrolidone, 1-methyl-3-[6-carbomethoxy-2-hexinyl-(1)]-4-[3-(RS)-hydroxy-4,4-dimethyl-5-allyloxy-(E)-1-pentenyl-(1)]-pyrrolidone, 1-methyl-3-[6-carbomethoxy-2-hexinyl-(1)]-4-[3-(RS)-hydroxy-4,4-dimethyl-5-isobutoxy-(E)-1-pentenyl-(1)]-pyrrolidone, 1-butyl-3-[6-carbomethoxy-2-hexinyl-(1)]-4-[3-(RS)-hydroxy-(E)-1-octenyl-(1)]-pyrrolidone, 1-butyl-3-[6-carbomethoxy-2-hexinyl-(1)]-4-[3-(RS)-hydroxy-(E)-1-decenyl-(1)]-pyrrolidone, 1-butyl-3-[6-carbomethoxy-2-hexinyl-(1)]-4-[3-(RS)-hydroxy-(E)-1-nonenyl-(1)]-pyrrolidone, 1-butyl-3-[6-carbomethoxy-2-hexinyl-(1)]-4-[3(RS)-hydroxy-(E)-1-hexenyl-(1)]-pyrroldione, 1-butyl-3-[6-carbomethoxy-2-hexinyl-(1)]-4-[3-(RS)-hydroxy-4,4-dimethyl-(E)-1-octenyl-(1)]-pyrrolidone, 1-butyl-3-[6-carbomethoxy-2-hexinyl-(1)]-4-[3-(RS)-hydroxy-4,4-dimethyl-5-ethoxy-(E)-1-pentenyl-(1)]-pyrrolidone, 1-butyl-3-[6-carbomethoxy-2-hexinyl-(1)]-4-[3-(RS)-hydroxy-3-cyclohexyl-(E)-1-propenyl-(1)]-pyrrolidone, 1-butyl-3-[6-carbomethoxy-2-hexinyl-(1)]-4-[3-(RS)-hydroxy-3-cycloheptyl-(E)-1-propenyl-(1)]-pyrrolidone, 1-butyl-3-[6-carbomethoxy-2-hexinyl-(1)]-4-[[3-(RS)-hydroxy-4-methyl-4-[4-(4-chlorophenoxy)-phenoxy]-(E)-1-butenyl-(1)]]-pyrrolidone, 1-butyl-3-[6-carbomethoxy-2-hexinyl-(1)]-4-[[3-(RS)-hydroxy-4,4-dimethyl-4-[4-(4-chlorophenoxy)-phenoxy]-(E)-1-butenyl-(1)]]-pyrrolidone, 1-butyl-3-[6-carbomethoxy-2-hexinyl-(1)]-4-[3-(RS)-hydroxy-4,4-dimethyl-5-methoxy-(E)-1-pentenyl-(1)]-pyrrolidone, 1-butyl-3-[6-carbomethoxy-2-hexinyl-(1)]-4-[3-(RS)-hydroxy-4,4-dimethyl-5-allyloxy-(E)-1-pentenyl-(1)]-pyrrolidone, 1-butyl-3-[6-carbomethoxy-2-hexinyl-(1)]-4-[3-(RS)-hydroxy-4,4-dimethyl-5-isobutoxy-(E)-1-pentenyl-(1)]-pyrrolidone, 1-butyl-3-[6-carbomethoxy-2-hexinyl-(1)]-4-[3-(RS)-hydroxy-5-ethylthio-(E)-1-pentenyl-(1)]-pyrrolidone, 1-butyl-3-[6-carbomethoxy-2-hexinyl-(1)]-4-[3-(RS)-hydroxy-4-(methyl-propionyl-amino)-(E)-1-butenyl-(1)]-pyrrolidone, 1-butyl-3-[6-carbomethoxy-2-hexinyl-(1)]-4-[3-(RS)-hydroxy-4-(4-fluorophenoxy)-(E)-1-butenyl-(1)]-pyrrolidone, 1-butyl-3-[6-carbomethoxy-2-hexinyl-(1)]-4-[3-(RS)-hydroxy-4-(4-chlorophenoxy)-(E)-1-butenyl-(1)]-pyrrolidone, 1-butyl-3-[6-carbomethoxy-2-hexinyl-(1)]-4-[3-(RS)-hydroxy-4-(3-trifluoromethylphenoxy)-(E)-1-butenyl-(1)]-pyrrolidone, 1-butyl-3-[6-carbomethoxy-2-hexinyl-(1)]-4-[3-(RS)-hydroxy-4-(3-chlorophenoxy)-(E)-1-butenyl-(1)]-pyrrolidone, 1-cyclohexyl-3-[6-carbomethoxy-2-hexinyl-(1)]-4-[3-(RS)-hydroxy-(E)-1-hexenyl-(1)]-pyrrolidone, 1-cyclohexyl-3-[6-carbomethoxy-2-hexinyl-(1)]-4-[3-(RS)-hydroxy-4,4-dimethyl-(E)-1-octenyl-(1)]-pyrrolidone, 1-[4-methyl-cyclohexyl(1)]-3-[6-carbomethoxy-2-hexinyl-(1)]-4-[3-(RS)-hydroxy-3-cyclohexyl-(E)-1-propenyl-(1)]-pyrrolidone, 1-[4-methyl-cyclohexyl(1)]-3-[6-carbomethoxy-2-hexinyl-(1)]-4-[3-(RS)-hydroxy-3-cycloheptyl-(E)-1-propenyl-(1)]-pyrrolidone, 1-cyclopentyl-3-[6-carbomethoxy-2-hexinyl-(1)]-4-[[3-(RS)-hydroxy-4-methyl-4-[4-(4-chlorophenoxy)-phenoxy-(E)-1-butenyl-(1)]]-pyrrolidone, 1-cycloheptyl-3-[6-carbomethoxy-2-hexinyl-(1)]-4-[[3-(RS)-hydroxy-4,4-dimethyl-4-[4-(4-chlorophenoxy)-phenoxy]-(E)-1-butenyl-(1)]]-pyrrolidone, 1-methyl-3-[6-carbomethoxy-hexyl-(1)]-4-[3-(RS)-hydroxy-(E)-1-hexenyl-(1)]-pyrrolidone, 1-methyl-3-[6-carbomethoxy-hexyl-(1)]-4-[3-(RS)-hydroxy-4,4-dimethyl-(E)-1-octenyl-(1)]-pyrrolidone, 1-methyl-3-[6-carbomethoxy-hexyl-(1)]-4-[3-(RS)-hydroxy-3-cyclohexyl-(E)-1-propenyl-(1)]-pyrrolidone, 1-methyl-3-[6-carbomethoxy-hexyl-(1)]-4-[3-(RS)-hydroxy-3-cycloheptyl-(E)-1-propenyl-(1)]-pyrrolidone, 1-methyl-3-[6-carbomethoxy-hexyl-(1)]-4-[[3-(RS)-hydroxy-4-methyl-4-[4-(4-chlorophenoxy)-phenoxy]-(E)-1-butenyl-(1)]]-pyrrolidone, 1-methyl-3-[6-carbomethoxy-hexyl-(1)]-4-[[3-(RS)-hydroxy-4,4-dimethyl-4-[4-(4-chlorophenoxy-phenoxy]-(E)-1-butenyl-(1)]]-pyrrolidone, 1-methyl-3-[6-carbomethoxy-hexyl-(1)]-4-[3-(RS)-hydroxy-5-ethylthio-(E)-1-pentenyl-(1)]-pyrrolidone, 1-methyl-3-[6-carbomethoxy-hexyl-(1)]-4-[3-(RS)-hydroxy-4-(4-fluorophenoxy)-(E)-1-butenyl-(1)]-pyrrolidone, 1-methyl-3-[6-carbomethoxy-hexyl-(1)]-4-[3-(RS)-hydroxy-4-(4-chlorophenoxy)-(E)-1-butenyl-(1)]-pyrrolidone, 1-methyl-3-[6-carbomethoxy-hexyl-(1)]-4-[3-(RS)-hydroxy-4-(3-trifluoromethylphenoxy)-(E)-1-butenyl-(1)]-pyrrolidone, 1-methyl-3-[6-carbomethoxy-hexyl-(1)]-4-[3-(RS)-hydroxy-4-(methyl-propionyl-amino)-(E)-1-butenyl-(1)]-pyrrolidone, 1-methyl-3-[6-carbomethoxy-hexyl-(1)]-4-[3-(RS)-hydroxy-4,4-dimethyl-5-ethoxy-(E)-1-pentenyl-(1)]-pyrrolidone, 1-methyl-3-[6-carbomethoxy-hexyl-(1)]-4-[3-(RS)-hydroxy-4,4-dimethyl-5-methoxy-(E)-1-pentenyl-(1)]-pyrrolidone, 1-methyl-3-[6-carbomethoxy-hexyl-(1)]-4-[3-(RS)-hydroxy-4,4-dimethyl-5-allyloxy-(E)-1-pentenyl-(1)]-pyrrolidone, 1-methyl-3-[6-carbomethoxy-hexyl-(1)]-4-[3-(RS)-hydroxy-4,4-dimethyl-5-isobutoxy-(E)-1-pentenyl-(1)]-pyrrolidone, 1-butyl-3-[6-carbomethoxy-hexyl-(1)]-4-[3-(RS)-hydroxy-(E)-1-octenyl-(1)]-pyrrolidone, 1-butyl-3-[6-carbomethoxy-hexyl-(1)]-4-[3-(RS)-hydroxy-(E)-1-decenyl-(1)]-pyrrolidone, 1-butyl-3-[6-carbomethoxy-hexyl-(1)]-4-[3-(RS)-hydroxy-(E)-1-nonenyl-(1)]-pyrrolidone, 1-butyl-3-[6-carbomethoxy-hexyl-(1)]-4-[3-(RS)-hydroxy-(E)-1-hexenyl-(1)]-pyrrolidone, 1-butyl-3-[6-carbomethoxy-hexyl-(1)]-4-[3-(RS)-hydroxy-4,4-dimethyl-(E)-1-octenyl-(1)]-pyrrolidone, 1-butyl-3-[6-carbomethoxy-hexyl-(1)]-4-[3-(RS)-hydroxy-4,4-dimethyl-5-ethoxy-(E)-1-pentenyl-(1)]-pyrrolidone, 1-butyl-3-[6-carbomethoxy-hexyl-(1)]-4-[3-(RS)-hydroxy-3-cyclohexyl-(E)-1-propenyl-(1)]-pyrrolidone, 1-butyl-3-[6-carbomethoxy-hexyl-(1)]-4-[3-(RS)-hydroxy-3-cycloheptyl-(E)-1-propenyl-(1)]-pyrrolidone, 1-butyl-3-[6-carbomethoxy-hexyl-(1)]-4-[[3-(RS)-hydroxy-4-methyl-4-[4-(4-chlorophenoxy)-phenoxy]-(E)-1-butenyl-(1)]]-pyrrolidone, 1-butyl-3-[6-carbomethoxy-hexyl-(1)]-4-[[3-(RS)-hydroxy-4,4-dimethyl-4-[4-(4-chlorophenoxy)-phenoxy]-(E)-1-butenyl-(1)]]-pyrrolidone, 1-butyl-3-[6-carbomethoxy-hexyl-(1)]-4-[3-(RS)-hydroxy-4,4-dimethyl-5-methoxy-(E)-1-pentenyl-(1)]-pyrrolidone, 1-butyl-3-[6-carbomethoxy-hexyl-(1)]-4-[3-(RS)-hydroxy-4,4-dimethyl-5-allyloxy-(E)-1-pentenyl-(1)]-pyrrolidone, 1-butyl-3-[6-carbomethoxy-hexyl-(1)]-4-[3-(RS)-hydroxy-4,4-dimethyl-5-isobutoxy-(E)-1-pentenyl-(1)]-pyrrolidone, 1-butyl-3-[6-carbomethoxy-hexyl-(1)]-4-[3-(RS)-hydroxy-5-ethylthio-1-pentenyl-(1)]-pyrrolidone, 1-butyl-3-[6-carbomethoxy-hexyl-(1)]-4-[3-(RS)-hydroxy-4-(methyl-propionyl-amino)-(E)-1-butenyl-(1)]-pyrrolidone, 1-butyl-3-[6-carbomethoxy-hexyl-(1)]-4-[3-(RS)-hydroxy-4-(4-fluorophenoxy)-(E)-1-butenyl-(1)]-pyrrolidone, 1-butyl-3-[6-carbomethoxy-hexyl-(1)]-4-[3-(RS)-hydroxy-4-(4-chlorophenoxy)-(E)-1-butenyl-(1)]-pyrrolidone, 1-butyl-3-[6-carbomethoxy-hexyl-(1)]-4-[3-(RS)-hydroxy-4-(3-trifluoromethylphenoxy)-(E)-1-butenyl-(1)]-pyrrolidone, 1-butyl-3-[6-carbomethoxy-hexyl-(1)]-4-[3-(RS)-hydroxy-4-(3-chlorophenoxy)-(E)-1-butenyl-(1)]-pyrrolidone, 1-cyclohexyl-3-[6-carbomethoxy-hexyl-(1)]-4-[3-(RS)-hydroxy-(E)-1-hexenyl-(1)]-pyrrolidone, 1-cyclohexyl-3-[6-carbomethoxy-hexyl-(1)]-4-[3-(RS)-hydroxy-4,4-dimethyl-(E)-1-octenyl-(1)]-pyrrolidone, 1-[4-methyl-cyclohexyl-(1)]-3-[6-carbomethoxy-hexyl-(1)]-4-[3-(RS)-hydroxy-3-cyclohexyl-(E)-1-propenyl-(1)]-pyrrolidone, 1-[4-methyl-cyclohexyl-(1)]-3-[6-carbomethoxy-hexyl-(1)]-4-[3-(RS)-hydroxy-3-cyclohexyl-(E)-1-propenyl-(1)]-pyrrolidone, 1-cyclopentyl-3-[6-carbomethoxy-hexyl-(1)]-4-[[3-(RS)-hydroxy-4-methyl-4-[4-(4-chlorophenoxy)-phenoxy]-(E)-1-butenyl-(1)]]-pyrrolidone, 1-cyclopentyl-3-[6-carbomethoxy-hexyl-(1)]-4-[[3-(RS)-hydroxy-4,4-dimethyl-4-[4-(4-chlorophenoxy)-phenoxy]-(E)-1-butenyl-(1)]]-pyrrolidone, 1-cyclopentyl-3-[6-carbomethoxy-hexyl-(1)]-4-[3-(RS)-hydroxy-5-ethylthio-(E)-1-pentenyl-(1)]-pyrrolidone, 1-cycloheptyl-3-[6-carbomethoxy-hexyl-(1)]-4-[3-(RS)-hydroxy-4-(4-fluorophenoxy)-(E)-1-butenyl-(1)]-pyrrolidone, 1-cycloheptyl-3-[6-carbomethoxy-hexyl-(1)]-4-[3-(RS)-hydroxy-4-(4-chlorophenoxy)-(E)-1-butenyl-(1)]-pyrrolidone, 1-methyl-3-[carbomethoxy-hexyl-(1)]-4-[3-(RS)-hydroxy-hexyl-(1)]-pyrrolidone, 1-methyl-3-[6-carbomethoxy-hexyl-(1)]-4-[3-(RS)-hydroxy-4,4-dimethyl-octyl-(1)]-pyrrolidone, 1-methyl-3-[6-carbomethoxy-hexyl-(1)]-4-[3-(RS)-hydroxy-3-cyclohexyl-propyl-(1)]-pyrrolidone, 1-methyl-3-[6-carbomethoxy-hexyl-(1)]-4-[3-(RS)-hydroxy-3-cycloheptyl-propyl-(1)]-pyrrolidone, 1-methyl-3-[6-carbomethoxy-hexyl-(1)]-4-[[3-(RS)-hydroxy-4-methyl-4-[4-(4-chlorophenoxy)-phenoxy]-butyl-(1)]]-pyrrolidone, 1-methyl-3-[6-carbomethoxy-hexyl-(1)]-4-[[3-(RS)-hydroxy-4,4-dimethyl-4-[4-(4-chlorophenoxy)-phenoxy]-butyl-(1)]]-pyrrolidone, 1-methyl-3-[6-carbomethoxy-hexyl-(1)]-4-[3-(RS)-hydroxy-5-ethylthio-pentyl-(1)]-pyrrolidone, 1-methyl-3-[6-carbomethoxy-hexyl-(1)]-4-[3-(RS)-hydroxy-4-(4-fluorophenoxy)-butyl-(1)]-pyrrolidone, 1-methyl-3-[6-carbomethoxy-hexyl-(1)]-4-[3-(RS)-hydroxy-4-(4-chlorophenoxy)-butyl-(1)]-pyrrolidone, 1-methyl-3-[6-carbomethoxy-hexyl-(1)]-4-[3-(RS)-hydroxy-4-(3-trifluoromethylphenoxy)-butyl-(1)]-pyrrolidone, 1-methyl-3-[6-carbomethoxy-hexyl-(1)]-4-[3-(RS)-hydroxy-4-(3-chlorophenoxy)-butyl-(1)]-pyrrolidone, 1-methyl-3-[6-carbomethoxy-hexyl-(1)]-4-[3-(RS)-hydroxy-4-(methyl-propionyl-amino)-butyl-(1)]-pyrrolidone, 1-methyl-3-[6-carbomethoxy-hexyl-(1)]-4-[3-(RS)-hydroxy-4,4-dimethyl-5-ethoxy-pentyl-(1)]-pyrrolidone, 1-methyl-3-[6-carbomethoxy-hexyl-(1)]-4-[3-(RS)-hydroxy-4,4-dimethyl-5-methoxy-pentyl-(1)]-pyrrolidone, 1-methyl-3-[6-carbomethoxy-hexyl-(1)]-4-[3-(RS)-hydroxy-4,4-dimethyl-5-allyloxy-pentyl-(1)]-pyrrolidone, 1-methyl-3-[6-carbomethoxy-hexyl-(1)]-4-[3-(RS)-hydroxy-4,4-dimethyl-5-isobutoxy-pentyl-(1)]-pyrrolidone 1-butyl-3-[6-carbomethoxy-hexyl-(1)]-4-[3-(RS)-hydroxy-nonyl-(1)]-pyrrolidone, 1-butyl-3-[6-carbomethoxy-hexyl-(1)]-4-[3-(RS)-hydroxy-hexyl-(1)]-pyrrolidone, 1-butyl-3-[6-carbomethoxy-hexyl-(1)]-4-[3-(RS)-hydroxy-4,4-dimethyloctyl-(1)]-pyrrolidone, 1-butyl-3-[6-carbomethoxy-hexyl-(1)]-4-[3-(RS)-hydroxy-4,4-dimethyl-5-ethoxy-pentyl-(1)]-pyrrolidone, 1-butyl-3-[6-carbomethoxy-hexyl-(1)]-4-[3-(RS)-hydroxy-3-cyclohexyl-propyl-(1)]-pyrrolidone, 1-butyl-3-[carbomethoxy-hexyl-(1)]-4-[3-(RS)-hydroxy-3-cycloheptyl-propyl-(1)]-pyrrolidone, 1-butyl-3-[6-carbomethoxy-hexyl-(1)]-4-[[3-(RS)-hydroxy-4-methyl-4-[4-(4-chlorophenoxy)-phenoxy]-butyl-(1)]]-pyrrolidone, 1-butyl-3-[6-carbomethoxy-hexyl-(1)]-4-[[3-(RS)-hydroxy-4,4-dimethyl-4-[4-(4-chlorophenoxy)-phenoxy]-butyl-(1)]]-pyrrolidone, 1-butyl-3-[6-carbomethoxy-hexyl-(1)]-4-[3-(RS)-hydroxy-4,4-dimethyl-5-methoxy-pentyl-(1)]-pyrrolidone, 1-butyl-3-[6-carbomethoxy-hexyl-(1)]-4-[3-(RS)-hydroxy-4,4-dimethyl-5-allyloxy-pentyl-(1)]-pyrrolidone, 1-butyl-3-[6-carbomethoxy-hexyl-(1)]-4-[3-(RS)-hydroxy-4,4-dimethyl-5-isobutoxy-pentyl-(1)]-pyrrolidone, 1-butyl-3-[6-carbomethoxy-hexyl-(1)]-4-[3-(RS)-hydroxy-5-ethylthio-pentyl-(1)]-pyrrolidone, 1-butyl-3-[6-carbomethoxy-hexyl-(1)]-4-[3-(RS)-hydroxy-4-(methyl-propionyl-amino)-butyl-(1)]-pyrrolidone, 1-butyl-3-[6-carbomethoxy-hexyl-(1)]-4-[3-(RS)-hydroxy-4-(4-fluorophenoxy)-butyl-(1)]-pyrrolidone, 1-butyl-3-[6-carbomethoxy-hexyl-(1)]-4-[3-(RS)-hydroxy-4-(4-chlorophenoxy)-butyl-(1)]-pyrrolidone, 1-butyl-3-[6-carbomethoxy-hexyl-(1)]-4-[3-(RS)-hydroxy-4-(3-trifluoromethylphenoxy)-butyl-(1)]-pyrrolidone, 1-cyclohexyl-3-[6-carbomethoxy-hexyl-(1)]-4-[3-(RS)-hydroxy-hexyl-(1)]-pyrrolidone, 1-cyclohexyl-3-[6-carbomethoxy-hexyl-(1)]-4-[3-(RS)-hydroxy-4,4-dimethyl-octyl-(1)]-pyrrolidone, 1-cyclopentyl-3-[6-carbomethoxy-hexyl-(1)]-4-[3-(RS)-hydroxy-3-cyclohexyl-propyl-(1)]-pyrrolidone, 1-cyclopentyl-3-[6-carbomethoxy-hexyl-(1)]-4-[3-(RS)-hydroxy-3-cycloheptyl-propyl-(1)]-pyrrolidone, 1-cyclopentyl-3-[6-carbomethoxy-hexyl-(1)]-4-[[3-(RS)-hydroxy-4-methyl-4-[4-(4-chlorophenoxy)-phenoxy]-butyl-(1)]]-pyrrolidone, 1-[4-methyl-cyclohexyl-(1)]-3-[6-carbomethoxy-hexyl-(1)]-4-[[3-(RS)-hydroxy-4,4-dimethyl-4-[4-(4-chlorophenoxy)-phenoxy]-butyl-(1)]]-pyrrolidone, 1-[4-methyl-cyclohexyl-(1)]-3-[6-carbomethoxy-hexyl-(1)]-4-[3-(RS)-hydroxy-5-ethylthio-pentyl-(1)]-pyrrolidone, 1-cycloheptyl-3-[6-carbomethoxy-hexyl-(1)]-4-[3-(RS)-hydroxy-4-(4-fluorophenoxy)-butyl-(1)]-pyrrolidone, 1-cycloheptyl-3-[6-carbomethoxy-hexyl-(1)]-4-[3-(RS)-hydroxy-4-(4-chlorophenoxy)-butyl-(1)]-pyrrolidone.

EXAMPLE 1

1-Methyl-3-[6-carbomethoxy-2-hexinyl-(1)]-4-hydroxymethylpyrrolidone a. At −70° C, 29.4 g (138 millimoles) of 1-methyl-4-(2-tetrahydropyranyl-oxymethyl)-pyrrolidone dissolved in 90 ml of diethylether were added within 20 minutes, while stirring, to 150 moles of LiN(i-C₃H₇)₂ in 150 ml of diethylether. After the solution had been stirred for another 45 minutes, it was filled into a dropping funnel which could be cooled (−35° to −40° C) and was added dropwise, while stirring, within 60 minutes, to a solution of 29.1 g (149 millimoles) of 1-bromo-6-chloro-hexine-(2) in 135 ml of ether, which solution was maintained at −70° C. After the solution had been stirred for another 90 minutes, it was slowly heated to room temperature, 75 ml of water were added dropwise, the organic phase was separated, and the aqueous phase was extracted three times with 50 ml of diethylether each. The combined ether phases were washed three times with 40 ml of cold 1N sulfuric acid each, once with 50 ml of saturated sodium-bicarbonate solution and once with 50 ml of water. After drying and concentrating in vacuo, 46.6 g of crude 1-methyl-3-[6-chloro-2-hexinyl-(1)]-4-(2-tetrahydropyranyl-oxymethyl)-pyrrolidone [$R_f$: 0.42 (ethylacetate)] were obtained from the organic phase, which was used in the following reaction step without further purification.

b. 7.5 Grams (153 millimoles) of sodium cyanide were introduced into 90 ml of DMSO and were heated to 80° C. 46.6 Grams (142.5 millimoles) of crude 1-methyl-3-[6-chloro-2-hexinyl-(1)]-4-(2-tetrahydropyranyl-oxymethyl)-pyrrolidone dissolved in 40 ml of DMSO were added dropwise, while stirring. Subsequently the reaction mixture was continued to be stirred for 3 to 6 hours at 80° C. The reaction progress was observed by way of thin-layer chromatography (ethylacetate). After the reaction has been completed, the mixture was cooled to 10° C, 200 ml of water were added and the aqueous phase was extracted three times with 200 ml of diethylether each. The combined ether phases were washed three times with saturated sodium chloride solution and were dried. After concentration in vacuo, 43.7 g of crude 1-methyl-3-[6-cyano-2-hexinyl-(1)]-4-(2-tetrahydropyranyl-oxymethyl)-pyrrolidone [$R_f$: 0.39 (ethylacetate)] were obtained which could be used in the following reaction without further purification.

c. 11 Grams (0.275 mole) of sodium hydroxide were dissolved in 33 ml of water, then 43.7 g (137.5 millimoles) of 1-methyl-3-[6-cyano-2-hexinyl-(1)]-4-(2-tetrahydropyranyloxymethyl)-pyrrolidone dissolved in 135 ml of ethyl alcohol were added, and the mixture was refluxed for 18 hours. Subsequently the alcohol was distilled off in vacuo, 150 ml of ice cold 2N sulfuric acid were added to the residue, while cooling with ice, and the product was extracted ten times with 10 ml of diethylether each. After drying and concentrating the combined ether phases, 47.4 g of crude 1-methyl-3-[6-carbohydroxy-2-hexinyl-(1)]-4-(2-tetrahydropyranyl-oxymethyl)-pyrrolidone were obtained, which were dissolved directly in 250 ml of methylene chloride and were mixed at 0° C with 380 ml of a 0.5 molar ethereal diazo methane solution. The reaction mixture was allowed to stand for 30 minutes at 0° C, and for 1 hour at room temperature. After concentration in vacuo, 43.7 g of crude 1-methyl-3-[6-carbomethoxy-2-hexinyl-(1)]-4-(2-tetrahydropyranyl-oxymethyl)-pyrrolidone [$R_f$: 0.45 (ethylacetate)] were obtained.

d. This product was dissolved in 200 ml of methanol, 3 drops of concentrated hydrochloric acid were added, and the mixture was refluxed for 75 minutes. After concentration in vacuo, the remaining oil was purified by way of column chromatography [silica gel/ethylacetate (for the separation of the by-products), then ethylacetate:ethanol = 10:1.5]. 25 Grams of 1-methyl-3-[6-carbomethoxy-2-hexinyl-(1)]-4-hydroxymethyl-pyrrolidone [$R_F$: 0.14 (ethylacetate)] were obtained.

$n_D^{20}$ = 1.5005 IR(CH$_2$Cl$_1$): $\nu$ = 3450 (OH), 1740 (C=O), 1690 (C=O) cm$^{-1}$ NMR: solvent: CDCl$_3$ N—CH$_3$: 2.82 ppm; O—CH$_3$: 3.64 ppm

EXAMPLE 2

1-Isopropyl-3-[6-carbomethoxy-2-hexinyl-(1)]-4-hydroxymethyl-pyrrolidone was obtained according to a method analogous to that of Example (1), starting from 1-isopropyl-4-(tetrahydropyranyl-oxymethyl)pyrrolidone.

$n_D^{20}$ = 1.4945 NMR: solvent: CDCl$_3$; O—CH$_3$: 3.63 ppm;

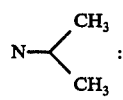

1.14 ppm;

4.23 ppm

EXAMPLE 3

1-n-Butyl-3-[6-carbomethoxy-2-hexinyl-(1)]-4-hydroxymethylpyrrolidone was obtained according to a method analogous to that of Example (1), starting from 1-n-butyl-4-(tetrahydropyranyl-oxymethyl)-pyrrolidone.

$n_D^{20}$ = 1.4855 NMR: solvent: CDCl$_3$; O—CH$_3$: 3.61 ppm; N/\/\CH$_3$: 0.9 ppm

EXAMPLE 4

1-Methyl-3-[6-carbomethoxy-2-hexinyl-(1)]-4-hydroxymethylpyrrolidone 29.1 Grams (91.5 millimoles) of 1-methyl-3-[6-cyano-2-hexinyl-(1)]-4-(2-tetrahydropyranyl-oxymethyl)-pyrrolidone were dissolved in 175 ml of diethylether and 90 ml of absolute methanol, the solution was saturated at 0° −5° C with hydrogen chloride and was continued to be stirred for about 2 to 3 hours at this temperature.

A test carried out by way of thin layer chromatography (silica gel, HCCl$_3$:CH$_3$OH = 90:10) revealed that the tetrahydropyrane radical was split off within a few minutes, and that the nitrile was converted completely into the imido-etherhydrochloride within 2 to 3 hours. Subsequently the excess hydrogen chloride and the solvent were eliminated in vacuo at a temperature of from 0° to 20° C. The residue was dissolved in 150 ml of methanol, and the solution was adjusted with aqueous sodium hydroxide solution of 33% strength, while cooling with ice, to a pH of from 1.5 to 2. In order to effect a complete hydrolysis of the imidoether-hydrochloride, the solution was refluxed for 50 to 60 minutes. For the working-up, the methanol was distilled off in vacuo, the residue was mixed with 50 ml of water, and the resulting ester was extracted with methylene chloride. The purification was carried out as in Example (1) by way of column chromatography.

19.1 Grams of 1-methyl-3-[6-carbomethoxy-2-hexinyl-(1)]-4-hydroxy-methyl-pyrrolidone were obtained.

The substance was identical with the one obtained according to Example 1.

EXAMPLE 5

1-Methyl-3-[6-carbomethoxy-2-hexinyl-(1)]-4-[3-oxo-(E)-1-octenyl-(1)]-pyrrolidone a. 8.3 Grams (83 millimoles) of chromium trioxide were introduced portionwise, at room temperature, into a well-stirred solution of 13.2 g (166 millimoles) of pyridine in 200 ml of methylene chloride. The mixture was continued to be stirred for 20 minutes at room temperature, was cooled to 0° C, and a solution of 2.67 g (10 millimoles) of 1-methyl-3-[6-carbomethoxy-2-hexinyl-(1)]-4-hydroxymethyl-pyrrolidone in 25 ml of absolute methylene chloride was added dropwise within 10 minutes. After another 30 minutes, 75 ml of 2N sulfuric acid were added, the organic phase was separated, was dried and evaporated in vacuo at a bath temperature not exceeding 30° C. 2.6 Grams of crude 1-methyl-3-[6-carbomethoxy-2-hexinyl-(1)]-4-formyl-pyrrolidone [$R_F$: 0.26 (ethylacetate)] were obtained, which were used in the following reaction without further purification.

b. A solution of 2.44 g (11 millimoles) of dimethyl-(2-oxoheptyl)-phosphonate in 30 ml of absolute dimethoxyethane was added dropwise, at room temperature, to a suspension of 0.29 g (12.5. millimoles) of sodium hydride in 70 ml of absolute dimethoxyethane. After the mixture had been stirred for 1.5 hours at 20° C, 2.6 g of crude 1-methyl-3-[6-carbomethoxy-2-hexinyl-(1)]-4-formyl-pyrrolidone were added dropwise. The mixture was continued to be stirred for 1.5 hours at 25° C, was acidified with 2N sulfuric acid (pH = 3 to 5), the solution was then concentrated in vacuo and the reaction product was extracted with diethylether. The purification of 1-methyl-3-[6-carbomethoxy-2-hexinyl-(1)]-4-[3-oxo-(E)-1-octenyl-(1)]-pyrrolidone was effected by way of column chromatography (silica gel; ethylacetate).

$R_F$: 0.56 (ethylacetate); IR(CH$_2$Cl$_2$): $\nu$ = 1740 (C=O), 1690 (C=O), 1640 (C=C) cm$^{-1}$

EXAMPLE 6

1-Methyl-3-[6-carbomethoxy-2-hexinyl-(1)]-4-[3-oxo-(E)-1-nonenyl-(1)]-pyrrolidone was obtained according to a method analogous to that of Example 5, by using dimethyl-(2-oxooctyl)-phosphate.

$R_F$: 0.57 (ethylacetate); IR(CH$_2$Cl$_2$): $\nu$ = 1750 (C=O), 1700 (C=O), 1640 (C=C) cm$^{-1}$

EXAMPLE 7

1-Methyl-3-[6-carbomethoxy-2-hexinyl-(1)]-4-[3-oxo-(E)-1-decenyl-(1)]-pyrrolidone was obtained according to a method analogous to that of Example 5, by using dimethyl-(2-oxononyl)-phosphonate.

$R_F$: 0.57 (ethylacetate); IR(CH$_2$Cl$_2$): $\nu$ = 1740 (C=O), 1700 (C=O), 1640 (C=C) cm$^{-1}$

EXAMPLE 8

1-Methyl-3-[6-carbomethoxy-2-hexinyl-(1)]-4-[3-oxo-4-(3-chlorophenoxy)-(E)-1-butenyl-(1)]-pyrrolidone was obtained according to a method analogous to that of Example 5, by using dimethyl-[2-oxo-3-(3-chlorophenoxy)-propyl]-phosphonate.

$R_F$: 0.55 (ethylacetate:methanol = 98:2)
IR(CH$_2$Cl$_2$): $\nu$ = 1730 (C=O), 1690 (C=O), 1630 (C=C) cm$^{-1}$

EXAMPLE 9

1-Methyl-3-[6-carbomethoxy-2-hexinyl-(1)]-4-[3-(RS)-hydroxy-(E)-1-octenyl-(1)]-pyrrolidone 15 milliliters of a 0.84 molar Zn(BH$_4$)$_2$ solution (12.5 millimoles) were added dropwise, at 0° C, to a solution of 1.0 g (2.77 millimoles) of 1-methyl-3-[6-carbomethoxy-2-hexinyl-(1)]-4-[3-oxo-(E)-1-octenyl-(1)]-pyrrolidone in 25 ml of absolute dimethoxyethane, and the mixture was continued to be stirred for 2.5 hours at room temperature. 5 Milliliters of 2N sulfuric acid were added (pH 5), the mixture was stirred for a short time and was buffered subsequently with saturated sodium bicarbonate solution to pH 7. The filtered solution was concentrated in vacuo, and the residue was extracted three times with 100 ml of methylene chloride each time. The organic phase was dried and was concentrated in vacuo. The remaining oil was purified by way of column chromatography (silica gel; ethylacetate).

$R_F$: 0.55 (HCCl$_3$:CH$_3$OH = 90:10) IR(CH$_2$Cl$_2$): $\nu$ = 3450 (OH), 1730 (C=O), 1690 (C=O) cm$^{-1}$

EXAMPLE 10

1-Methyl-3-[6-carbomethoxy-2-hexinyl-(1)]-4-[3-(RS)-hydroxy-(E)-1-nonenyl-(1)]-pyrrolidone was obtained according to a method analogous to that of Example 9, by using the product of Example 6 as starting compound.

$R_F$: 0.28 (ethylacetate) IR(CH$_2$Cl$_2$): $\nu$ = 3450 (OH), 1740 (C=O), 1690 (C=O) cm$^{-1}$

EXAMPLE 11

1-Methyl-3-[6-carbomethoxy-2-hexinyl-(1)]-4-[3-(RS)-hydroxy-(E)-1-decenyl-(1)]-pyrrolidone was obtained according to a method analogous to that of Example 9, by using the product of Example 7 as starting compound.

$R_F$: 0.29 (ethylacetate) IR(CH$_2$Cl$_2$): $\nu$ = 3450 (OH), 1740 (C=O), 1690 (C=O) cm$^{-1}$

EXAMPLE 12

1-Methyl-3-[6-carbomethoxy-2-hexinyl-(1)]-4-[3-(RS)-hydroxy-4-(3-chlorophenoxy)-(E)-1-butenyl-(1)]-pyrrolidone was obtained according to a method analogous to that of Example 9, by using the product of Example 8 as starting compound.

$R_F$: 0.33 (ethylacetate) IR(CH$_2$Cl$_2$): $\nu$ = 3420 (OH), 1730 (C=O), 1680 (C=O) cm$^{-1}$

EXAMPLE 13

1-Methyl-3-[6-carbohydroxy-2-hexinyl-(1)]-4-[3-(RS)-hydroxy-(E)-1-octenyl-(1)]-pyrrolidone 0.64 Gram (1.83 millimoles) of 1-methyl-3-[6-carbomethoxy-2-hexinyl-(1)]-4-[3-(RS)-hydroxy-(E)-1-octenyl-(1)]-pyrrolidone from Example 9 was dissolved in a mixture of 2.5 ml of 1N NaOH, 5 ml of methanol and 5 ml of dimethoxyethane, and the mixture was stirred for 5 hours at room temperature. It was then acidified with concentrated hydrochloric acid (pH = 1), the product was extracted five times with 50 ml of methylene chloride each time, the organic phase was dried over sodium sulfate and was concentrated. The desired compound was obtained in the form of a colorless viscous oil.

$R_F$: 0.34 (HCCl$_3$:CH$_3$OH = 90:10) IR(CH$_2$Cl$_2$): $\nu$ = 3100 – 3500 (OH), 1730 (C=O), 1680 (C=O) cm$^{-1}$

EXAMPLE 14

1-Methyl-3-[6-carbohydroxy-2-hexinyl-(1)]-4-[3-(RS)-hydroxy-(E)-1-nonenyl-(1)]-pyrrolidone was obtained according to a method analogous to that of Example 13, by using the product of Example 10 as starting compound.

$R_F$: 0.35 (CHCl$_3$:CH$_3$OH = 90:10) IR(CH$_2$Cl$_2$): $\nu$ = 3000 – 3500 (OH), 1720 (C=O), 1680 (C=O) cm$^{-1}$

EXAMPLE 15

1-Methyl-3-[6-carbohydroxy-2-hexinyl-(1)]-4-[3-(RS)-hydroxy-(E)-1-decenyl-(1)]-pyrrolidone was obtained according to a method analogous to that of Example 13, by using the product of Example 11 as starting compound.

$R_F$: 0.58 (CHCl$_3$:C$_2$H$_5$OH = 80:20) IR(CH$_2$Cl$_2$): $\nu$ = 3100 – 3450 (OH), 1735 (C=O), 1690 (C=O) cm$^{-1}$

EXAMPLE 16

1-Methyl-3-[6-carbohydroxy-2-hexinyl-(1)]-4-[3-(RS)-hydroxy-4-(3-chlorophenoxy)-(E)-1-butenyl-(1)]-pyrrolidone was obtained according to a method analogous to that of Example 13, by using the product of Example 12 as starting compound.

$R_F$: 0.35 (CHCl$_3$:CH$_3$OH = 90:10) IR(CH$_2$Cl$_2$): 3000 – 3500 (OH), 1730 (C=O), 1680 (C=O) cm$^{-1}$

EXAMPLE 17

1-Methyl-3-[6-carbomethoxy-hexyl-(1)]-4-hydroxymethyl-pyrrolidone 5.4 Grams (20 millimoles) of 1-methyl-3-[6-carbomethoxy-2-hexinyl-(1)]-4-hydroxymethyl-pyrrolidone were dissolved in a hydrogenation vessel in 50 ml of methanol, and 200 mg of palladium/coal (9.7% of Pd) were added. At a temperature of from 24° to 26° C, hydrogen was introduced, while stirring thoroughly. After about 1.5 to 2 hours, 890 ml of hydrogen were used up, and the reaction came to a stop. For the working-up, the catalyst was filtered off with suction, washed out with methanol, and the filtrate was concentrated in vacuo. 5.1 Grams of pure 1-methyl-3-[6-carbomethoxy-hexyl-(1)]-4-hydroxy-methyl-pyrrolidone were obtained as residue.

$R_F$: 0.15 (ethylacetate) $n_D^{20}$ = 1.4898 IR(CH$_2$Cl$_2$): $\nu$ = 3450 (OH), 1735 (C=O), 1690 (C=O) cm$^{-1}$

EXAMPLE 18

1-Butyl-3-[6-carbomethoxy-hexyl-(1)]-4-hydroxymethyl-pyrrolidone was obtained according to a method analogous to that of Example 17, if 1-butyl-3-[6-carbomethoxy-2-hexinyl-(1)]-4-hydroxymethyl-pyrrolidone was used as starting compound.

$R_F$: 0.45 (ethylacetate) IR(CH$_2$Cl$_2$): $\nu$ = 3450 (OH), 1730 (C=O), 1690 (C=O) cm$^{-1}$

EXAMPLE 19

1-Isopropyl-3-[6-carbomethoxy-hexyl-(1)]-4-hydroxymethyl-pyrrolidone was obtained according to a method analogous to that of Example 17, if 1-isopropyl-3-[6-carbomethoxy-2-hexinyl-(1)]-4-hydroxymethyl-pyrrolidone was used as starting compound.

$R_F$: 0.35 (ethylacetate) IR(CH$_2$Cl$_2$): $\nu$ = 3450 (OH), 1730 (C=O), 1690 (C=O) cm$^{-1}$

EXAMPLE 20

1-Methyl-3-[6-carbomethoxy-hexyl-(1)]-4-[3-oxo-(E)-1-octenyl-(1)]-pyrrolidone a. 8.3 Grams (83 millimoles) of chromium trioxide were introduced portionwise, at room temperature, into a well-stirred solution of 13.2 g (166 millimoles) of pyridine in 200 ml of methylene chloride. The mixture was continued to be stirred for 20 minutes at room temperature, was then cooled to 0° C, and a solution of 2.71 g (10 millimoles) of 1-methyl-3-[6-carbomethoxy-hexyl-(1)]-4-hydroxymethyl-pyrrolidone in 25 ml of absolute methylene chloride was added dropwise within 10 minutes. After another 30 minutes, 75 ml of 2N sulfuric acid were added, the organic phase was separated, dried and evaporated in vacuo at a bath temperature not exceeding 30° C. 2.7 Grams of crude 1-methyl-3-[6-carbomethoxy-hexyl-(1)]-4-formyl-pyrrolidone [$R_F$: 0.26 (ethylacetate)] were obtained which was used in the following reaction without further purification.

b. A solution of 2.44 g (11 millimoles) of dimethyl-2-oxoheptyl)-phosphonate in 30 ml of absolute dimethoxyethane was added dropwise, at room temperature, to a suspension of 0.29 g (12.5 millimoles) of sodium hydride in 70 ml of absolute dimethoxyethane. After the mixture had been stirred for 1.5 hours at 20° C, 2.7 g of crude 1-methyl-3-[6-carbomethoxy-hexyl-(1)]-4-formyl-pyrrolidone were added dropwise. The mixture was then stirred for another 1.5 hours at 25° C, was acidified with 2N sulfuric acid (pH = 3 - 5), the solution was concentrated in vacuo, and the reaction product was extracted with diethylether. The purification of 1-methyl-3-[6-carbomethoxy-hexyl-(1)-4-[3-oxo-(E)-1-octenyl-(1)]-pyrrolidone was effected by way of column chromatography (silica gel; ethyl acetate).

$R_F$: 0.56 (ethyl acetate) IR(CH$_2$Cl$_2$): $\nu$ = 1740 (C=O), 1690 (C=O), 1640 (C=C) cm$^{-1}$

EXAMPLE 21

1-Methyl-3-[6-carbomethoxy-hexyl-(1)]-4-[3-oxo-(E)-1-nonenyl-(1)]-pyrrolidone was obtained according to a method analogous to that of Example 20, by using dimethyl-(2-oxooctyl)-phosphonate.

$R_F$: 0.56 (ethylacetate) IR(CH$_2$Cl$_2$): $\nu$ = 1750 (C=O), 1700 (C=O), 1640 (C=C) cm$^{-1}$

EXAMPLE 22

1-Methyl-3-[6-carbomethoxy-hexyl-(1)]-4-[3-oxo-(E)-1-decenyl-(1)]-pyrrolidone was obtained according to a method analogous to that of Example 20, by using dimethyl-(2-oxononyl)-phosphonate.

$R_F$: 0.57 (ethylacetate) IR(CH$_2$Cl$_2$): $\nu$ = 1740 (C=O), 1700 (C=O), 1640 (C=C) cm$^{-1}$

EXAMPLE 23

1-Methyl-3-[6-carbomethoxy-hexyl-(1)]-4-[3-oxo-4-(3-chlorophenoxy)-(E)-1-butenyl-(1)]-pyrrolidone was obtained according to a method analogous to that of Example 20, by using dimethyl-[2-oxo-3-(3-chlorophenoxy)-propyl]-phosphonate.

$R_F$: 0.55 (ethylacetate:methanol = 98:2) IR(CH$_2$Cl$_2$): $\nu$ = 1730 (C=O), 1690 (C=O), 1630 (C=C) cm$^{-1}$

EXAMPLE 24

1-Methyl-3-[6-carbomethoxy-hexyl-(1)]-4-[3-(RS)-hydroxy-(E)-1-octenyl-(1)]-pyrrolidone 15 milliliters of a 0.84 molar Zn(BH$_4$)$_2$ solution (12.5 millimoles) were added dropwise, at 0° C, to a solution of 1.0 g (2.74 millimoles) of 1-methyl-3-[6-carbomethoxy-hexyl-(1)]-4-[3-oxo-(E)-1-octenyl-(1)]-pyrrolidone in 25 ml of absolute dimethoxyethane, and the mixture was stirred for 2.5 hours at room temperature. Subsequently, 5 ml of a 2N sulfuric acid (pH 5) were added, the mixture was continued to be stirred for a short time and was then buffered with a saturated sodium bicarbonate solution to a pH value of 7. The filtered solution was concentrated in vacuo, and the residue was extracted three times with 100 ml of methylene chloride each.

The organic phase was dried and concentrated in vacuo. The remaining oil was purified by way of column chromatography (silica gel; ethylacetate).

$R_{F_1}$: 0.42; $R_{F_2}$: 0.32 (ethylacetate) IR(CH$_2$Cl$_2$): $\nu$ = 3450 (OH), 1740 (C=O), 1690 (C=O) cm$^{-1}$

EXAMPLE 25

1-Methyl-3-[6-carbomethoxy-hexyl-(1)]-4-[3-(RS)-hydroxy-(E)-1-nonenyl-(1)]-pyrrolidone was obtained according to a method analogous to that of Example 24, if the product of Example 5 was used as starting compound.

$R_{F_1}$: 0.44; $R_{F_2}$: 0.36 (ethylacetate) IR(CH$_2$Cl$_2$): $\nu$ = 3450 (OH), 1740 (C=O), 1690 (C=O) cm$^{-1}$

EXAMPLE 26

1-Methyl-3-[6-carbomethoxy-hexyl-(1)]-4-[3-(RS)-hydroxy-(E)-1-decenyl-(1)]-pyrrolidone was obtained according to a method analogous to that of Example 24, if the product of Example 22 was used as starting compound.

$R_{F_1}$: 0.44; $R_{F_2}$: 0.35 (ethylacetate) IR(CH$_2$Cl$_2$): $\nu$ = 3450 (OH), 1735 (C=O), 1690 (C=O) cm$^{-1}$

EXAMPLE 27

1-Methyl-3-[6-carbomethoxy-hexyl-(1)]-4-[3-(RS)-hydroxy-4-(3-chlorophenoxy)-(E)-1-butenyl-(1)]-pyrrolidone was obtained according to a method analogous to that of Example 24, if the product of Example 23 was used as starting compound.

$R_F$: 0.39 (ethylacetate) IR(CH$_2$Cl$_2$): $\nu$ = 3450 (OH), 1730 (C=O), 1680 (C=O) cm$^{-1}$

EXAMPLE 28

1-Methyl-3-[6-carbohydroxy-hexyl-(1)]-4-[3-(RS)-hydroxy-(E)-1-octenyl-(1)]-pyrrolidone 0.64 Gram (1.74 millimoles) of 1-methyl-3-[6-carbomethoxy-hexyl-(1)]-4-[3-(RS)-hydroxy-(E)-1-octenyl-(1)]-pyrrolidone was dissolved in a mixture of 2.5 ml of 1N NaOH, 5 ml of methanol and 5 ml of dimethoxyethane, and the whole was stirred for 5 hours at room temperature. The reaction mixture was acidified with concentrated hydrochloric acid (pH = 1), the product was extracted five times with 50 ml of methylene chloride each, the organic phase was dried over sodium sulfate and was concentrated. The desired compound was obtained in the form of a colorless viscous oil.

$R_F$: 0.31 ($HCCl_3$:$CH_3OH$ = 90:10) IR($CH_2Cl_2$): $\nu$ = 3100 - 3500 (OH), 1735 (C=O), 1690 (C=O) $cm^{-1}$

EXAMPLE 29

1-Methyl-3-[6-carbohydroxy-hexyl-(1)]-4-[3-(RS)-hydroxy-(E)-1-nonenyl-(1)]-pyrrolidone was obtained according to a method analogous to that of Example 28, if the product of Example 25 was used as starting compound.

$R_F$: 0.39 ($CHCl_3$:$CH_3OH$ = 90:10) IR($CH_2Cl_2$): $\nu$ = 3000 - 3500 (OH), 1720 (C=O), 1690 (C=O) $cm^{-1}$

EXAMPLE 30

1-Methyl-3-[6-carbohydroxy-hexyl-(1)]-4-[3-(RS)-hydroxy-(E)-1-decenyl-(1)]-pyrrolidone was obtained according to a method analogous to that of Example 28, if the product of Example 26 was used as starting compound.

$R_F$: 0.60 ($CHCl_3$:$C_2H_5OH$ = 80:20) IR($CH_2Cl_2$) $\nu$ = 3100 - 3450 (OH), 1730 (C=O), 1690 (C=O) $cm^{-1}$

EXAMPLE 31

1-Methyl-3-[6-carbohydroxy-hexyl-(1)]-4-[3-(RS)-hydroxy-4-(3-chlorophenoxy)-(E)-1-butenyl-(1)]-pyrrolidone was obtained according to a method analogous to that of Example 28, if the product of Example 27 was used as starting compound.

$R_F$: 0.36 ($CHCl_3$:$CH_3OH$ = 90:10) IR($CH_2Cl_2$): $\nu$ = 3000 - 3500 (OH), 1725 (C=O), 1680 (C=O) $cm^{-1}$

EXAMPLE 32

1-Butyl-3-[6-carbomethoxy-hexyl-(1)]-4-[3-(RS)-hydroxy-octyl-(1)]-pyrrolidone 0.65 Gram (1.6 millimoles) of 1-butyl-3-[6-carbomethoxy-(Z)-2-hexenyl-(1)]-4-[3-(RS)-hydroxy-(E)-1-octenyl-(1)]-pyrrolidone was dissolved in 20 ml of methanol, and 80 mg of palladium/coal (9.7% of Pd) were added. At a temperature of from 23° to 26° C, hydrogen was introduced, while the mixture was being stirred thoroughly. After the absorption of hydrogen had been completed, the catalyst was filtered off with suction, was washed out with methanol, and the filtrate was concentrated in vacuo. The residue was purified by way of column chromatography (silica gel; ethylacetate). 1-Butyl-3-[6-carbomethoxy-hexyl-(1)]-4-[3-(RS)-hydroxy-octyl-(1)]-pyrrolidone was obtained in the form of a viscous colorless oil.

$R_F$: 0.73 (ethylacetate) IR($CH_2Cl_2$): $\nu$ = 3450 (OH), 1740 (C=O), 1680 (C=O) $cm^{-1}$

EXAMPLE 33

1-Butyl-3-[6-carbomethoxy-hexyl-(1)]-4-[3-(RS)-hydroxy-decyl-(1)]-pyrrolidone was obtained according to a method analogous to that of Example 32, if 1-butyl-3-[6-carbomethoxy-(Z)-2-hexenyl-(1)]-4-[3-(RS)-hydroxy-(E)-1-decenyl-(1)]-pyrrolidone was used as starting compound.

$R_F$: 0.75 (ethylacetate) IR($CH_2Cl_2$): $\nu$ = 3450 (OH), 1740 (C=O), 1680 (C=O) $cm^{-1}$

EXAMPLE 34

1-Butyl-3-[6-carbomethoxy-hexyl-(1)]-4-[3-(RS)-hydroxy-4-(3-chloro-phenoxy)-butyl-(1)]-pyrrolidone was obtained according to a method analogous to that of Example 32, if 1-butyl-3-[6-carbomethoxy-(Z)-2-hexenyl-(1)]-4-[3-(RS)-hydroxy-4-(3-chlorophenoxy)-(E)-1-butenyl-(1)]-pyrrolidone was used as starting compound.

$R_F$: 0.30 (diethylether) IR($CH_2Cl_2$): $\nu$ = 3450 (OH), 1730 (C=O), 1680 (C=O) $cm^{-1}$

EXAMPLE 35

1-Methyl-3-[6-carbomethoxy-hexyl-(1)]-4-[3-(RS)-hydroxy-octyl-(1)]-pyrrolidone was obtained according to a method analogous to that of Example 32, if 1-methyl-3-[6-carbomethoxy-2-hexinyl-(1)]-4-[3-(RS)-hydroxy-(E)-1-octenyl-(1)]-pyrrolidone was used as starting compound.

$R_F$: 0.30 (ethylacetate) IR($CH_2Cl_2$): $\nu$ = 3450 (OH), 1740 (C=O), 1680 (C=O) $cm^{-1}$

EXAMPLE 36

1-Methyl-3-[6-carbomethoxy-hexyl-(1)]-4-[3-(RS)-hydroxy-nonyl-(1)]-pyrrolidone was obtained according to a method analogous to that of Example 32, if 1-methyl-3-[6-carbomethoxy-2-hexinyl-(1)]-4-[3-(RS)-hydroxy-(E)-1-nonenyl-(1)]-pyrrolidone was used as starting compound.

$R_F$: 0.35 (ethylacetate) IR($CH_2CL_2$): $\nu$ = 3450 (OH), 1740 (C=O), 1680 (C=O) $cm^{-1}$

EXAMPLE 37

1-Methyl-3-[6-carbomethoxy-hexyl-(1)]-4-[3-(RS)-hydroxy-decyl-(1)]-pyrrolidone was obtained according to a method analogous to that of Example 32, if 1-methyl-3-[6-carbomethoxy-2-hexinyl-(1)]-4-[3-(RS)-hydroxy-(E)-1-decenyl-(1)]-pyrrolidone was used as starting compound.

$R_F$: 0.35 (ethylacetate) IR($CH_2Cl_2$): $\nu$ = 3450 (OH), 1740 (C=O), 1680 (C=O) $cm^{-1}$

EXAMPLE 38a

1-Methyl-3-[6-carbomethoxy-hexyl-(1)]-4-[3-oxo-octyl-(1)]-pyrrolidone was obtained according to a method analogous to that of Example 32, if 1-methyl-3-[6-carbomethoxy-2-hexinyl-(1)]-4-[3-oxo-(E)-1-octenyl-(1)]-pyrrolidone was used as starting compound.

$R_F$: 0.57 (ethylacetate) IR($CH_2Cl_2$): $\nu$ = 1735 (C=O), 1690 (C=O) $cm^{-1}$

EXAMPLE 38b

1-Methyl-3-[6-carbomethoxy-hexyl-(1)]-4-[3-(RS)-hydroxy-octyl-(1)]-pyrrolidone 15 milliliters of a 0.84 molar $Zn(BH_4)_2$ solution (12.5 millimoles) were added dropwise at 0° C to a solution of 1.0 g (2.72 millimoles) of 1-methyl-3-[6-carbomethoxy-hexyl-(1)]-4-[3-oxo-octyl-(1)]-pyrrolidone in 25 ml of absolute dimethoxyethane, and the mixture was continued to be stirred for 2.5 hours at room temperature. Subsequently, 5 ml of 2N sulfuric acid were added (pH 5), then the mixture was again stirred and was buffered afterwards with saturated sodium bicarbonate solution to a pH value of 7. The filtered solution was concentrated in vacuo, and the residue was extracted three times with 100 ml of methylene chloride each. The organic phase was dried and concentrated in vacuo. The remaining oil was purified by way of column chromatography (silica gel, ethylacetate).

$R_f$: 0.30 (ethylacetate) IR(CH$_2$CL$_2$): $\nu$ = 3450 (OH), 1740 (C=O), 1680 (C=O) cm$^{-1}$

EXAMPLE 39a

1-Butyl-3-[6-carbomethoxy-hexyl-(1)]-4-[3-oxo-octyl-(1)]-pyrrolidone was obtained according to a method analogous to that of Example 32, if 1-butyl-3-[6-carbomethoxy-2-hexinyl-(1)]-4-[3-oxo-(E)-1-octenyl-(1)]-pyrrolidone was used as starting compound.

$R_f$: 0.83 (ethylacetate) IR(CH$_2$Cl$_2$): $\nu$ = 1740 (C=O), 1690 (C=O) cm$^{-1}$

EXAMPLE 39b

1-Butyl-3-[6-carbomethoxy-hexyl-(1)]-4-[3-(RS)-hydroxy-octyl-(1)]-pyrrolidone was obtained according to a method analogous to that of Example 38b from the product obtained according to Example 39a.

$R_f$: 0.72 (ethylacetate) IR(CH$_2$Cl$_2$): $\nu$ = 3450 (OH), 1740 (C=O), 1680 (C=O) cm$^{-1}$

EXAMPLE 40

1-Methyl-3-[6-carbomethoxy-hexyl-(1)]-4-[3-oxo-octyl-(1)]-pyrrolidone was obtained according to a method analogous to that of Example 32, if 1-methyl-3-[6-carbomethoxy-hexyl-(1)]-4-[3-oxo-(E)-1-octenyl-(1)]-pyrrolidone was used as starting compound.

$R_f$: 0.57 (ethylacetate) IR(CH$_2$Cl$_2$): $\nu$ = 1735 (C=O), 1690 (C=O) cm$^{-1}$

EXAMPLE 41

1-Methyl-3-[6-carbohydroxy-hexyl-(1)]-4-[3-(RS)-hydroxy-octyl-(1)]-pyrrolidone 0.64 Gram (1.735 millimoles) of 1-methyl-3-[6-carbomethoxy-hexyl-(1)]-4-[3-(RS)-hydroxy-octyl-(1)]-pyrrolidone was dissolved in a mixture of 2.5 ml of 1N NaOH, 5 ml of methanol and 5 ml of dimethoxy-ethane, and the whole was stirred for 5 hours at room temperature. The mixture was acidified with concentrated hydrochloric acid (pH = 1), the product was extracted five times with 50 ml of methylene chloride each, the organic phase was dried over sodium sulfate and was concentrated. The desired compound was obtained in the form of a colorless viscous oil.

$R_f$: 0.32 (HCCl$_3$:CH$_3$OH = 90:10) IR(CH$_2$Cl$_2$): $\nu$ = 3100 – 3500 (OH), 1720 (C=O), 1690 (C=O) cm$^{-1}$

EXAMPLE 42

1-Butyl-3-[6-carbohydroxy-hexyl-(1)]-4-[3-(RS)-hydroxy-octyl-(1)]-pyrrolidone was obtained according to a method analogous to that of Example 41.

$R_f$: 0.50 (HCCl$_3$:CH$_3$OH = 90:10) IR(CH$_2$Cl$_2$): $\nu$ = 3100 – 3500 (OH), 1725 (C=O), 1690 (C=O) cm$^{-1}$

We claim:
1. A compound of the formula

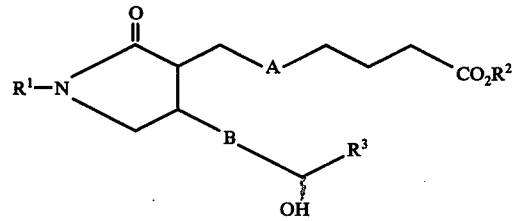

wherein the side chains in the 3- and 4- positions on the pyrrolidone ring are in trans-position with respect to each other, and physiologically acceptable metal and amine salts of the acid defined when R$^2$ is hydrogen, wherein A is —C≡C— and B is —CH=CH—, or
A is —CH$_2$—CH$_2$— and B is —CH$_2$—CH$_2$—, or
A is —CH$_2$—CH$_2$— and B is —CH=CH—, and
R$^1$ is straight-chain or branched alkyl having 1 to 6 carbon atoms, cycloalkyl having from 3 to 7 ring members, or cycloalkyl having 3 to 7 ring members mono-substituted by alkyl or alkoxy having 1 to 4 carbon atoms; R$^2$ is hydrogen, aliphatic hydrocarbon having 1 to 5 carbon atoms, or cycloaliphatic or araliphatic hydrocarbon having 3 to 8 carbon atoms; and R$^3$ is cycloalkyl having 3 to 7 ring members, phenyl, furyl, straight-chain or branched alkyl having 1 to 10 carbon atoms, or straight-chain or branched alkyl having 1 to 10 carbon atoms mono-substituted by
  (a) O-alkyl or S-alkyl having 1 to 5 carbon atoms,
  (b) phenoxy or phenoxy mono-substituted by
    (i) alkyl having 1 to 3 carbon atoms
    (ii) haloalkyl having 1 to 3 carbon atoms
    (iii) halogen
    (iv) phenoxy, or
    (v) halophenoxy
  (c) O-furyl or O-benzyl, or
  (d) trifluoromethyl.

2. A pharmaceutical composition for the treatment of bronchial spasms, hypertension, or the secretion of excess gastric juice, which composition comprises a therapeutically-effective amount of a compound or salt as in claim 1 in combination with a pharmaceutically acceptable carrier.

3. A method for treating bronchial spasms, hypertension, or the secretion of excess gastric juice in a patient suffering therefrom which comprises administering to said patient a therapeutically-effective amount of a compound as in claim 1.

* * * * *